United States Patent
Sloman

(10) Patent No.: US 6,925,329 B1
(45) Date of Patent: Aug. 2, 2005

(54) AUTOMATIC SETTING OF CARDIAC OPERATING PARAMETERS BASED UPON CAPTURE THRESHOLD LEVEL

(75) Inventor: Laurence S. Sloman, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 373 days.

(21) Appl. No.: 09/929,681

(22) Filed: Aug. 13, 2001

(51) Int. Cl.[7] ............................................. A61N 1/362
(52) U.S. Cl. ................................................. 607/9
(58) Field of Search .......................... 600/509, 510; 607/4, 5, 7, 9, 11, 27, 28

(56) References Cited

U.S. PATENT DOCUMENTS

| | | | |
|---|---|---|---|
| 4,590,941 A | * 5/1986 | Saulson et al. | 128/419 PG |
| 4,686,988 A | * 8/1987 | Sholder | 128/419 PT |
| 4,708,142 A | * 11/1987 | DeCote, Jr. | 128/419 PT |
| 4,712,555 A | * 12/1987 | Thornander et al. | 128/419 PG |
| 4,729,376 A | * 3/1988 | DeCote, Jr. | 128/419 PT |
| 4,788,980 A | * 12/1988 | Mann et al. | 128/419 PG |
| 4,940,052 A | * 7/1990 | Mann et al. | 128/419 PG |
| 4,944,298 A | * 7/1990 | Sholder | 128/419 PG |
| 4,969,460 A | * 11/1990 | Callaghan et al. | 128/419 PG |
| 4,969,467 A | * 11/1990 | Callaghan et al. | 128/419 PG |
| 4,974,589 A | * 12/1990 | Sholder | 607/9 |
| 5,031,616 A | * 7/1991 | Mann et al. | 128/419 PG |
| 5,127,402 A | * 7/1992 | Mann et al. | 128/419 PT |
| 5,228,439 A | * 7/1993 | Mann et al. | 128/419 PG |
| 5,318,593 A | * 6/1994 | Duggan | 607/9 |
| 5,350,410 A | * 9/1994 | Kleks et al. | 607/28 |
| 5,417,718 A | * 5/1995 | Kleks et al. | 607/28 |
| 5,466,254 A | * 11/1995 | Helland | 607/123 |
| 5,554,174 A | * 9/1996 | Causey, III | 607/5 |
| 5,573,550 A |   11/1996 | Zadeh et al. | 607/28 |
| 5,685,315 A |   11/1997 | McClure et al. | 128/708 |

* cited by examiner

*Primary Examiner*—Jeffrey R. Jastrzab
*Assistant Examiner*—Frances P. Oropeza

(57) ABSTRACT

An apparatus and method for operating an implantable stimulation device are disclosed. The implantable stimulation device is configured to dynamically modify pacing pulse energies based upon a patient's varying capture threshold. In at least certain situations where the implantable stimulation device modifies the pacing pulse energy, a stored value for an operating parameter, such as a ventricular blanking period or a maximum sensor rate, is automatically adjusted based upon the new pacing pulse energy. Additionally, the stored value may also be adjusted by additional variables in combination with the new pacing pulse energy.

22 Claims, 7 Drawing Sheets

FIG. 4

| AUTO CAPTURE ADJUSTED PARAMETER | PARAMETER PROGRAMMED |
|---|---|
| ATRIAL PULSE AMPLITUDE | VENTRICULAR BLANKING PERIOD VENTRICULAR SAFETY STANDBY |
| | MAXIMUM SENSOR RATE |
| | VENTRICULAR REFRACTORY PERIOD ATRIAL REFRACTORY PERIOD (PVARP) |
| | ATRIAL SENSITIVITY VENTRICULAR SENSITIVITY |
| | ATRIAL LEAD SUPERVISION (ON/OFF) |
| | A. FAST RECHARGE A. BLOCK OVERLAP |

400 — 402, 404, 406, 408, 410, 412

| AUTO CAPTURE ADJUSTED PARAMETER | PARAMETER PROGRAMMED |
|---|---|
| VENTRICULAR PULSE AMPLITUDE | MAXIMUM SENSOR RATE |
| | PVAB |
| | VENTRICULAR REFRACTORY PERIOD ATRIAL REFRACTORY PERIOD (PVARP) |
| | ATRIAL SENSITIVITY VENTRICULAR SENSITIVITY |
| | VENTRICULAR LEAD SUPERVISION (ON/OFF) |
| | V. FAST RECHARGE V. BLOCK OVERLAP |

450 — 452, 454, 456, 458, 460, 462

| ATRIAL PULSE AMPLITUDE | VENTRICULAR BLANKING PERIOD |
|---|---|
| 0.5 V | 4 ms |
| 1.0 V | 4 ms |
| 1.5 V | 4 ms |
| 2.0 V | 12 ms |
| 3.0 V | 12 ms |
| 4.0 V | 16 ms |
| 5.0 V | 24 ms |
| 6.0 V | 28 ms |
| 7.0 V | 32 ms |
| 7.5 V | 39 ms |

FIG. 5

| BATTERY IMPEDANCE | MAXIMUM SENSOR RATE | | |
|---|---|---|---|
| | 0 TO 1 V | 1 V TO 4 V | GREATER THAN 4 V |
| LESS THAN 500 ohms | NO CHANGE | REDUCE BY 30 ms | REDUCE BY 60 ms |
| 500 TO 2000 ohms | REDUCE BY 70 ms | REDUCE BY 100 ms | REDUCE BY 130 ms |
| 2000 to 5000 ohms | REDUCE BY 170 ms | REDUCE BY 200 ms | REDUCE BY 230 ms |
| GREATER THAN 5000 ohms | REDUCE BY 220 ms | REDUCE BY 250 ms | REDUCE BY 280 ms |

FIG. 6

| PULSE AMPLITUDE | REFRACTORY PERIOD |
|---|---|
| 0.5 V | NORMAL |
| 1.0 V TO 4.0 V | NORMAL |
| 4.25 V TO 5.0 V | INCREASE BY 25ms |
| GREATER THAN 5.0 V | INCREASE BY 50ms |

FIG. 7

| PULSE AMPLITUDE | SENSITIVITY |
|---|---|
| 0 TO 1 V | NORMAL (0.1 TO 2 mv) |
| 1 V TO 4 V | MINIMUM 0.5 mv |
| GREATER THAN 4 V | MINIMUM 1.0 mv |

FIG. 8

AUTOMATIC SETTING OF CARDIAC OPERATING PARAMETERS BASED UPON CAPTURE THRESHOLD LEVEL

FIELD OF INVENTION

This invention relates generally to implantable cardiac stimulation devices, including both single chamber and multi-chamber pacemakers, defibrillators, cardioverters and combinations thereof, and more particularly to a system and method for automatically setting operating parameters based upon a current stimulation output energy.

DESCRIPTION OF RELATED ART

Implantable cardiac stimulation devices, such as pacemakers and implantable cardioverter-defibrillators (ICDs), are devices that are implanted within the body of a patient so as to correct and regulate heart function. Typically, these devices include one or more leads that are adapted to be implanted within the body of the patient so as to be adjacent and/or attached to the heart in order to deliver therapeutic electrical stimulation pulses to the heart. Typically, these devices also include a control unit having a microprocessor that is positioned within a casing (or "housing") that is also adapted to be implanted within the body of the patient.

Implantable cardiac stimulation devices have inherent and significant size limitations. The space within the casing is usually at a premium because the overall size of the implanted casing is preferably kept as small as possible to fit inside the patient's body while also minimizing patient discomfort. A conventional stimulation device casing accommodates a processor, circuitry for producing therapeutic waveforms, memory devices for storing data, and a battery to supply power.

Because these stimulation devices are implanted within the patient, a surgical procedure is required. When the battery within a stimulation device approaches the end of its useful life, the patient typically must undergo another surgical procedure to implant a new stimulation device. More operations mean greater risks to patient health and increased costs, not to mention patient inconvenience and discomfort. Therefore, it is highly desirable to extend the life span of stimulation devices whenever, and as much as, possible.

Many paths have been taken in an attempt to extend stimulation device life span. For example, one path has been to monitor battery level and limit the extent to which high power modes of operation may be used during low battery periods. Examples of this type of approach are described in U.S. Pat. Nos.: U.S. Pat. No. 5,228,439 entitled "System and Method for Maintaining Proper Device Operation at Battery Depletion by Self-Regulating Current Drain Usage"; U.S. Pat. No. 5,127,402 entitled "System and Method for Maintaining Stimulation Pulse Amplitude at Battery Depletion by Self-Regulating Current Drain Usage"; U.S. Pat. No. 5,031,616 entitled "Implantable Stimulation Device Having Means for Self-Regulating Current Drain Usage at Battery Depletion."

As these patents indicate, the life span of most stimulation devices is dictated primarily by the rate at which battery power is consumed. Thus, a substantial effort has been directed toward minimizing the amount of energy used by stimulation devices, while ensuring that the devices continue to deliver effective therapy. One such effort has been the introduction of mechanisms that set the pacing pulse output energy at a level just above the patient's capture threshold.

The capture threshold is the minimum amount of electrical stimulation that effectively evokes a cardiac contraction in a particular patient. By automatically evaluating the patient's capture threshold during normal operation, and adjusting the pacing pulse energy accordingly, the stimulation device is able to extend battery life, often significantly. The output energy of the normal stimulation pulse may be adjusted by changing the pulse width, changing the pulse amplitude, or changing both the pulse width and the pulse amplitude. Common examples of such capture tracking systems are the AutoCapture™ systems and methods, available from St. Jude Medical, Inc.

A traditional AutoCapture™ system senses an electrical post-stimulus signal in the heart and compares this signal with a stored value or set of values. If there exists sufficient correlation between the value or values and the post-stimulus signal, this indicates that a true evoked response has been sensed, and thus the heart has been "captured" by the stimulus signal (i.e. the stimulus signal caused the heart chamber to contract). If such correlation is not found, a loss of capture state is presumed and a large backup pulse (e.g. 4.5 volts) is delivered to the heart within the refractory period of the tissue, thereby ensuring patient safety. Typically, a loss-of-capture routine is invoked that increases the output energy of the stimulation pulse by a prescribed amount in an effort to obtain capture.

One such system and method is described in U.S. Pat. No. 5,350,410 (the "'410 patent") entitled "Autocapture System for Implantable Pulse Generator" (Kleks et al.), which is hereby incorporated by reference as if set forth fully herein. The '410 patent discloses a capture verification test for determining the value or values and the sensitivity settings that yield capture. In addition, the '410 patent discloses an automatic threshold setting routine for automatically setting the output energy of the normal stimulation pulse. Thus, typical capture tracking systems allow reduced power usage for implantable pacemakers and ICDs, without compromising patient safety.

While conventional capture tracking systems do reduce power usage by automatically setting the pacing pulse output energy, they fail to address other programmable parameters that affect the operation of implantable pacemakers and ICDs. For example, many implantable stimulation devices define a programmable blanking period or interval, which is the period of time, after delivery of an output pulse, during which the sense amplifier of the pulse generator is temporarily disabled. In systems with high polarization leads, the polarization artifact on the lead electrode during this period is so large that attempting to sense the evoked response is ineffective. Additionally, in dual-chamber stimulation devices, the blanking interval is utilized to prevent inappropriate detection of signals in one chamber that emanate from another chamber (i.e. crosstalk).

Over time, the control units of implantable stimulation devices have become increasingly sophisticated, thereby allowing the control units to tailor the therapeutic electrical stimulation that is provided to the heart to optimize device performance and heart regulation. These implantable stimulation devices typically incorporate numerous sensors that provide data to the control unit, enabling the control unit to optimize the therapeutic stimulation provided to the heart. These devices also typically include numerous programmable parameters that enable physician control of how the therapeutic stimulation is optimized.

Despite the above-described improvements in both programmability and energy conservation of implantable stimulation devices, further improvements are still needed.

Specifically, many of the programmable features that have been added to modern stimulation devices have simply been added to the existing architecture, without consideration of the automatically adjusting stimulation pulse energies.

Accordingly, the shortcomings associated with the related art have heretofore not been adequately addressed. The present invention addresses such problems by providing a system and method that have not previously been proposed.

SUMMARY OF INVENTION

It is an object of this invention to enable improvement in implantable stimulation device performance by providing a method and apparatus for extending device longevity and/or improving delivery of effective therapy. In one aspect, the invention comprises a method for operating an implantable cardiac stimulation device, which dynamically modifies pacing pulse energies. In at least certain situations where the device modifies a pacing pulse energy, a value for an operating parameter is automatically adjusted based upon the new pacing pulse energy.

In one embodiment, the value for the operating parameter is automatically adjusted based upon an additional variable. For example, in one embodiment, the operating parameter is a maximum sensor rate, which is adjusted based upon the new pacing pulse energy level and a measure of current battery usage. Alternative embodiments include alternative operating parameters, which may be adjusted individually or collectively in various devices. These alternative parameters include, but are not limited to, the ventricular blanking period and/or the ventricular safety standby, ventricular refractory and/or atrial refractory period, post-ventricular atrial blanking period (PVAB), atrial and/or ventricular sensitivity, atrial and/or ventricular lead supervision, atrial fast recharge and/or atrial block overlap, and the like.

In another aspect, the invention is directed to an implantable stimulation device that includes a pulse generator; cardiac sensing circuitry; and a control unit coupled with the pulse generator and the cardiac sensing circuitry. The control unit is configured to adjust a pacing pulse output energy in response to a change in a patient's capture threshold. The control unit is further configured to modify a value for an operating parameter in at least certain situations where the pacing pulse output energy has been changed, such that the new value is based upon the new pacing pulse energy.

In one embodiment, the implantable stimulation device further comprises a memory, and the control unit comprises a microcontroller and a control program. Additionally, in one embodiment, the value for the operating parameter is modified by the control unit based upon an additional variable, in combination with the pacing pulse output energy.

Further features and advantages of the invention as well as the structure and operation of various embodiments of the invention are described in detail below with reference to the accompanying drawings.

BRIEF DESCRIPTION OF FIGURES

The features and advantages of the present invention may be more readily understood by reference to the following description, taken in conjunction with the accompanying drawings, in which:

FIG. 4 is one illustrative embodiment of two programmed parameter groupings that are used by an automatic operating parameter setting control program in an implantable stimulation device according to one embodiment of the invention;

FIG. 5 is an illustration of a parameter value table that is used by an automatic operating parameter setting control program in an implantable stimulation device to adjust the ventricular blanking period according to one embodiment of the invention;

FIG. 6 is an illustration of a parameter value table that is used by an automatic operating parameter setting control program in an implantable stimulation device to adjust maximum sensor rate according to one embodiment of the invention;

FIG. 7 is an illustration of a parameter value table that is used by an automatic operating parameter setting control program in an implantable stimulation device to adjust refractory periods according to one embodiment of the invention; and FIG. 8 is an illustration of a parameter value table that is used by an automatic operating parameter setting control program in an implantable stimulation device to adjust sensitivity settings according to one embodiment of the invention.

DETAILED DESCRIPTION OF INVENTION

The present invention is directed to a system and method for automatically setting one or more operating parameters in an implantable cardiac stimulation device based upon an automatically adjusted stimulation pulse output energy, for example, in a device that utilizes an automatic capture threshold algorithm to periodically adjust the stimulation pulse energy. The following description is of various embodiments of the invention and the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
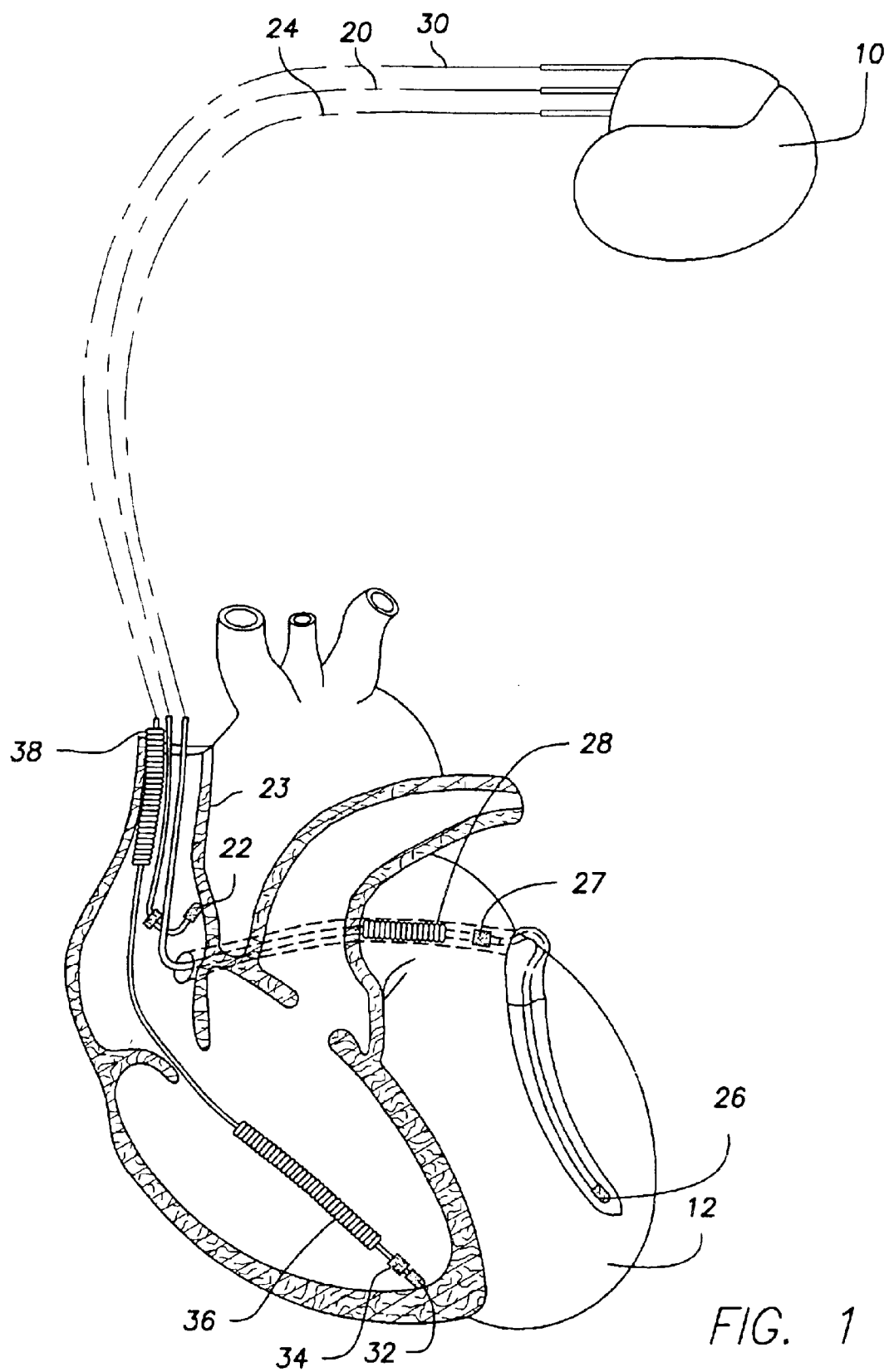
FIG. 1 is a diagram illustrating an implantable stimulation device in electrical communication with three leads implanted into a patient's heart for delivering multi-chamber stimulation and shock therapy according to one embodiment of the invention.

FIG. 1 is a diagram illustrating an implantable stimulation device 10 in electrical communication with three leads 20, 24, and 30 that are implanted into a patient's heart for delivering multi-chamber stimulation and shock therapy according to one embodiment of the invention. The present invention may be used with as few as one lead and may also be used for pacing any of the four chambers of the heart. The number of leads used, and the location(s) of attachment to the heart, will depend on the particular patient's condition as is well known in the relevant art(s). For example, in one dual-chamber pacing embodiment, the implantable stimulation device includes two leads that are adapted to be positioned within the right atrium and the right ventricle of the heart, respectively, so as to enable delivery of pacing pulses and sensing of heart activity in both the right atrium and right ventricle.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, stimulation device 10 is coupled to an implantable right atrial lead 20 having an atrial tip electrode 22, which typically is implanted in the patients right atrial appendage. Moreover, the implantable right atrial lead 20 includes an atrial ring electrode 23 located relatively near the atrial tip electrode 22. This proximity enables localized bipolar sensing of an evoked response within the right atrium of the heart 12, thereby reducing sensing of extraneous myopotentials, as is well understood in the art. In addition, this proximity enables sensing of an evoked response with the atrial ring electrode 23. In general, at least one electrode used in the sensing vector is located relatively close to the electrode used to deliver the stimulation pulse.

Each electrode used for both delivery of stimulation pulses and sensing of evoked responses is preferably designed to reduce polarization on the electrode. Such polarization reducing designs include increased surface geometry and specialized electrode coatings, as is well known in the art.

To sense left atrial and ventricular cardiac signals and to provide left chamber pacing therapy, stimulation device 10 is preferably coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible via the coronary sinus.

Accordingly, an exemplary coronary sinus lead 24 is designed to receive atrial and ventricular cardiac signals and to deliver left ventricular pacing therapy using a left ventricular tip electrode 26, left atrial pacing therapy using a left atrial ring electrode 27, and shocking therapy using a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. The right ventricular ring electrode 34 is located relatively near the right ventricular tip electrode 32. This proximity enables localized bipolar sensing of an evoked response within the right ventricle of the heart 12, thereby reducing sensing of extraneous myopotentials, as is well understood in the art. In addition, this proximity enables sensing of an evoked response with the right ventricular ring electrode 34. In general, at least one electrode used in the sensing vector is located relatively close to the electrode used to deliver the stimulation pulse.

Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
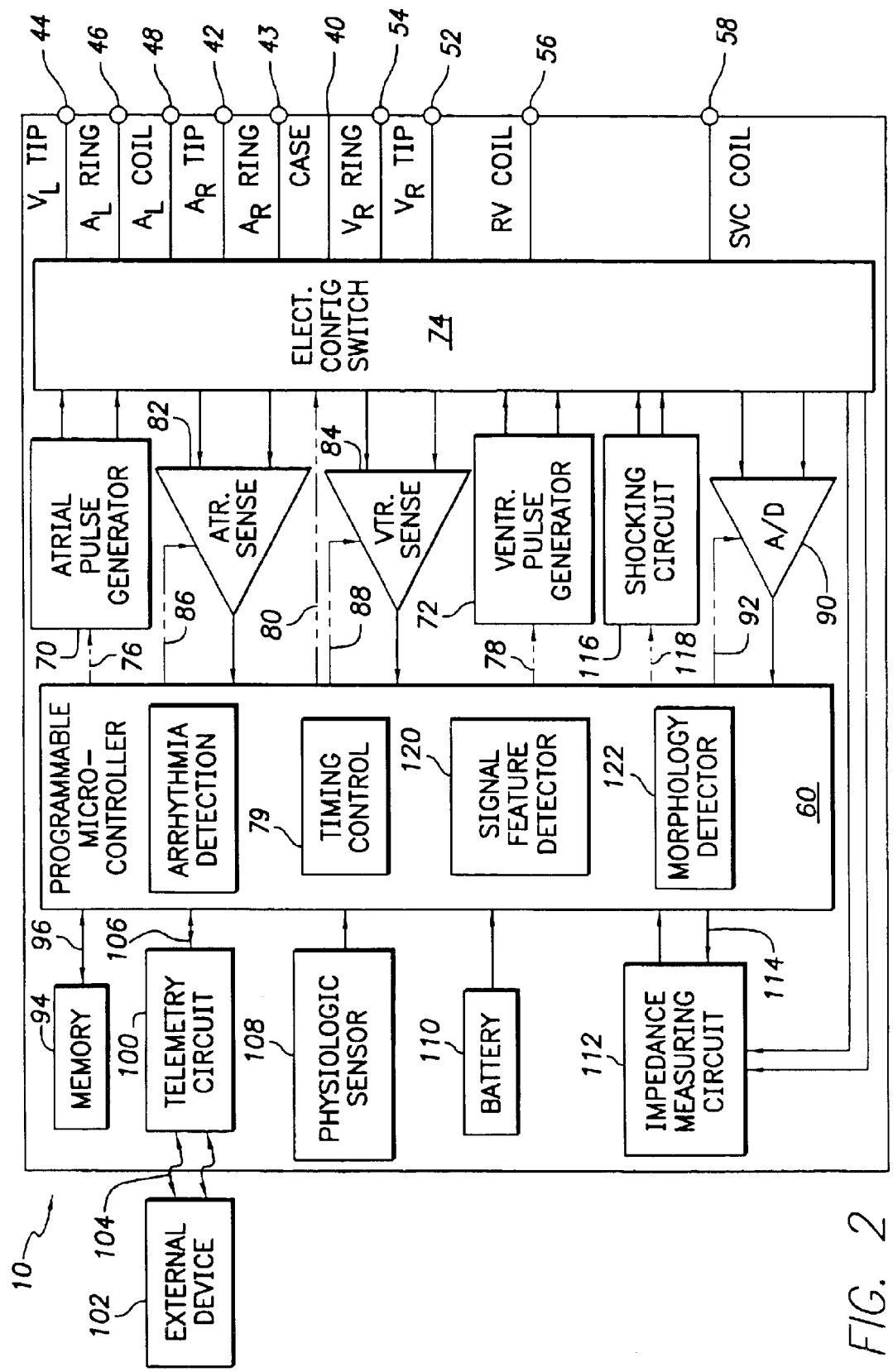
FIG. 2 is a functional block diagram of a multi-chamber implantable stimulation device illustrating the basic elements of a stimulation device that can provide cardioversion, defibrillation and pacing stimulation in multiple chambers of the heart according to one embodiment of the invention.

FIG. 2 is a functional block diagram of one embodiment of a multi-chamber implantable stimulation device 10 illustrating the basic elements of a stimulation device that can provide cardioversion, defibrillation and pacing stimulation in four chambers of the heart according to one embodiment of the invention. As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes a right atrial tip terminal ($A_R$ TIP) 42 adapted for connection to the atrial tip electrode 22 and a right atrial ring terminal ($A_R$ RING) 43 adapted for connection to the atrial ring electrode 23.

To achieve left chamber sensing, pacing and shocking, the connector includes a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the invention include the microprocessor-based control system of U.S. Pat. No. 4,940,052, entitled "Microprocessor Controlled Rate-responsive Pacemaker Having Automatic Rate Response Threshold Adjustment" (Mann et al.), the state-machine of U.S. Pat. No. 4,712,555, entitled "Physiologically Responsive Pacemaker and Method of Adjusting the Pacing Interval Thereof" (Thornander et al.), and U.S. Pat. No. 4,944,298, entitled "Atrial Rate Based Programmable Pacemaker with Automatic Mode Switching Means" (Sholder). For a more detailed description of the various timing intervals used within the stimulation device and their inter-relationship, see U.S. Pat. No. 4,788,980, entitled "Pacemaker Having PVC Response and PMT Terminating Features" (Mann et al.). The '052, '555, '298 and '980 patents are hereby incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 that is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., all of which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. Moreover, the switch 74 preferably includes at least one small resistor for electrically connecting a lead electrode, which has been used to deliver a stimulation pulse, with the case 40, thereby enabling rapid reduction of polarization on the stimulation electrode prior to using that same electrode for sensing an evoked response.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing low amplitude signal characteristics of atrial or ventricular fibrillation.

For a complete description of a typical sensing circuit, see U.S. Pat. No. 5,573,550, entitled "Implantable Stimulation Device having a Low Noise, Low Power, Precision Amplifier for Amplifying Cardiac Signals" (Zadeh et al.). For a complete description of an automatic gain control system, see U.S. Pat. No. 5,685,315, entitled "Cardiac Arrhythmia Detection System for an Implantable Stimulation Device" (McClure et al.). Accordingly, the '550 and the '315 patents are hereby incorporated herein by reference.

The outputs of the atrial and ventricular sensing circuits, 82 and 84, are connected to the microcontroller 60 which, in turn, is able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Preferably, the data acquisition system 90 is coupled with the microcontroller 60, and/or other detection circuitry, for detecting an evoked response and/or a lead polarization signal from the heart 12 in response to an applied stimulus, thereby aiding in the detection of "capture" and "loss-of-capture" (LOC). In an alternative embodiment, the data acquisition system 90 is built into the microcontroller 60, whereby digital signals representative of cardiac activity are generated by a control program designed to sample atrial and/or ventricular cardiac signals acquired by the atrial and ventricular sensing circuits, 82 and 84.

Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on a detection feature, such as the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See for example, U.S. Pat. No. 4,729,376, entitled "Cardiac Pacer and Method Providing Means for Periodically Determining Capture Threshold and Adjusting Pulse Output Level Accordingly" (Decote, Jr.); U.S. Pat. No. 4,708,142, entitled "Automatic Cardiac Capture Threshold Determination System and Method" (Decote, Jr.); U.S. Pat. No. 4,686,988, entitled "Pacemaker System and Method for Measuring and Monitoring Cardiac Activity and for Determining and Maintaining Capture" (Sholder); and U.S. Pat. No. 4,969,467, entitled "Pacemaker with Improved Automatic Output Regulation" (Callaghan et al.). The '376, '142, '988, and '467 patents are hereby incorporated herein by reference.

As will be described in greater detail below, the stimulation device 10 is adapted to be able to adjust various parameters of the stimulation device 10 based upon a determined capture threshold. It will be appreciated from the following discussion that the manner in which the stimulation device 10 adjusts its various parameters can be used in any of a number of different implantable cardiac stimulation devices without departing from the spirit of the present invention.

The microcontroller 60 is further coupled to a memory 94 by a suitable data/address bus 96. The microcontroller 60 uses the memory 94 for storage of control data used in controlling the operation of the stimulation device 10. The control data comprises programmable operating parameters, which can be stored and modified, as needed, to customize the operation of the stimulation device 10 for a particular patient. Such operating parameters define, for example, pacing pulse amplitude, pulse duration, electrode polarity, rate, sensitivity, signal sampling, automatic features, arrhythmia detection criteria, and the amplitude, waveshape and vector of each shocking pulse to be delivered to the patient's heart 12 within each respective tier of therapy. In addition, other variable operating parameters may be stored by microcontroller 60, such as ventricular blanking periods, maximum sensor rate, post-ventricular atrial refractory period (PVARP), post-ventricular atrial blanking period (PVAB), atrial and/or ventricular sensitivity, and the like, as is described in more detail below.

The microcontroller 60 also uses the memory 94 for periodic recording of historical data acquired by the data acquisition system 90. This historical data comprises both patient data and device data. Thus a treating physician may use this historical data to review the performance of the implanted stimulation device 10 and the function of the heart 12 during follow-up visits. This historical data may also be used for subsequent analysis to guide the programming of the stimulation device 10, either by a human programmer or by the stimulation device 10 itself.

Advantageously, the historical data may be noninvasively downloaded from memory 94 and the operating parameters of the implantable device 10 may be noninvasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller 60 by way of a control signal 106. The telemetry circuit 100 advantageously allows intracardiac electrograms and status information relating to the operation of the device 10 (as contained in the microcontroller 60 or memory 94) to be sent to the external device 102 through an established communication link 104. Examples of this established communication link 104 include an electromagnetic telemetry link and a remote communication link such as a pair of modems interconnected via a telecommunications link and equipped with telemetry capabilities.

In alternative embodiments, the stimulation device 10 includes one or more physiologic sensors 108, such as activity sensors, minute ventilation sensors, and the like. These physiologic sensors 108 are commonly referred to as "rate-responsive" sensors because they are typically used to adjust pacing stimulation rate according to the exercise state of the patient. However, the physiological sensors 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

While shown as being included within the stimulation device 10, it is to be understood that the physiologic sensors 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the present invention and is shown only for completeness.

The stimulation device additionally includes a battery 110 that provides operating power to all of the circuits shown in FIG. 2. In an embodiment of the stimulation device 10 that employs shocking therapy, the battery 110 is preferably capable of operating at low current drains for long periods of time, and of providing high-current pulses (for capacitor charging) when the patient requires a shock pulse. In this embodiment, the battery 110 also preferably has a predictable discharge characteristic so that elective replacement time can be detected. Accordingly, in one embodiment, the device 10 preferably employs lithium/silver vanadium oxide batteries, as is true for most (if not all) current devices.

In one embodiment, the stimulation device 10 further includes magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

In another alternative embodiment, the device 10 includes an impedance measuring circuit 112, which is enabled by the microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 byway of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV coil electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The operation of the stimulation device 10 is generally controlled by a control program stored in the memory 94 and executed by the microcontroller 60. In one embodiment, this control program comprises multiple integrated program modules, with each module bearing responsibility for controlling one or more functions of the stimulation device 10. For example, one program module may control the delivery of stimulating pulses to the heart 12, while another may control the verification of ventricular capture and the determination of ventricular pacing energy output. As shown, the capture verification module may include a signal feature detector module 120 and a morphology detector module 122. In effect, each program module is a control program dedicated to a specific function or set of functions of the stimulation device 10.

Figure 3:
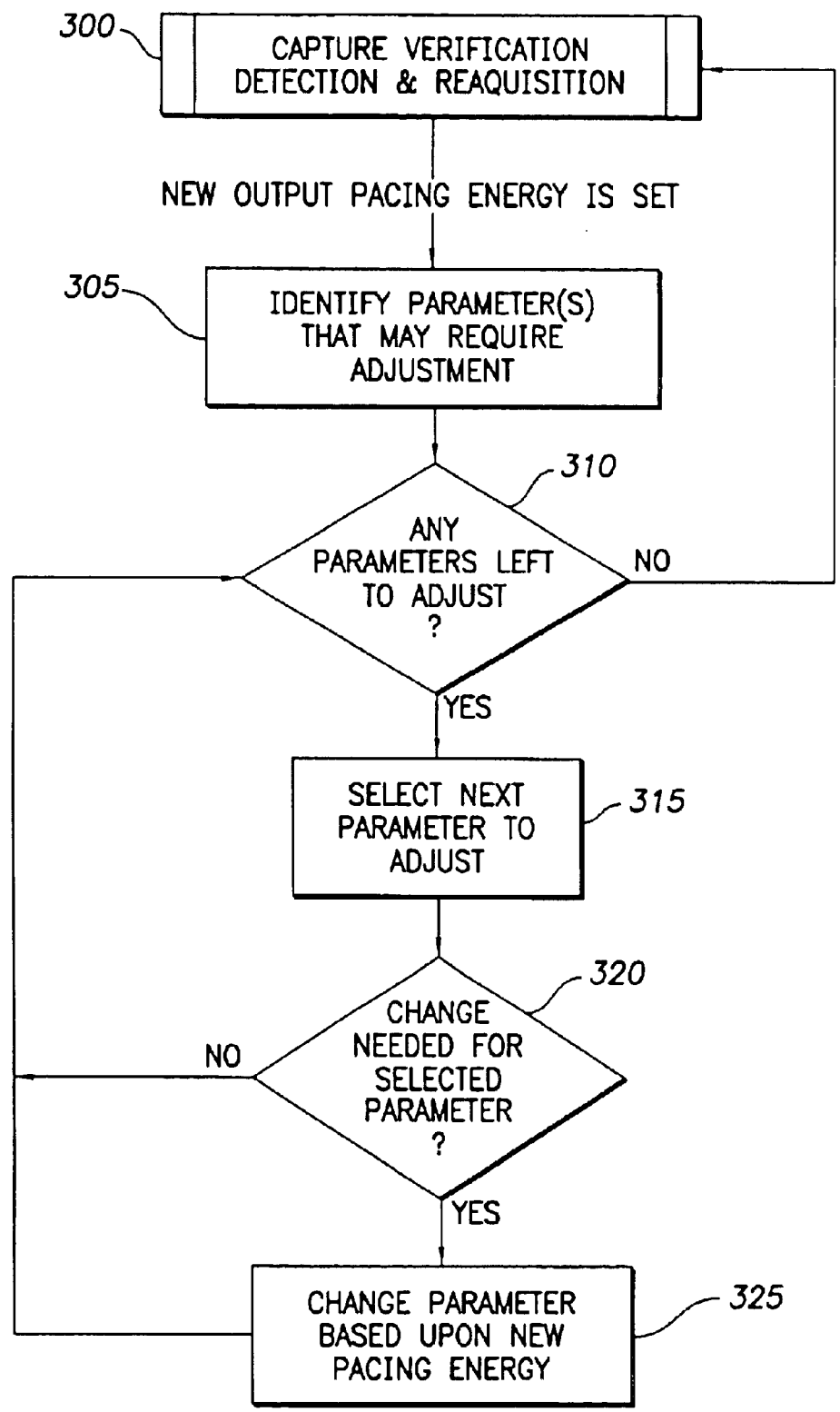
FIG. 3 is a logic flow diagram of an automatic operating parameter setting control program executed by a microcontroller in an implantable stimulation device according to one embodiment of the invention.

FIG. 3 is a logic flow diagram of a program for automatically setting one or more operating parameters that is executed by microcontroller 60 in implantable stimulation device 10 according to one embodiment of the invention. Referring now to FIG. 3, operation begins at step 300, in which capture verification, detection, and reacquisition steps are performed by microcontroller 60. The present invention may be implemented with any implantable device that is operative to adjust pacing pulse energy dynamically in response to a patient's changing capture threshold. In general, however, dynamic adjustment of pacing energy involves three main processes: (1) capture verification, (2) capture detection, and (3) capture reacquisition.

Capture verification is a process by which the efficiency of the current pacing pulse energy is assessed. Typically, this involves periodically lowering the pacing pulse energy in incremental steps until capture is lost, then raising the pacing pulse energy to a level slightly above the last setting where capture was detected, thereby including a small safety margin in the output energy. Capture verification helps to ensure that a selected pacing pulse energy does not remain unnecessarily high when a patient's capture threshold lowers. The present invention may be used with any number of capture verification methods and systems, including those not yet developed, such as those in which a patient's capture threshold is assessed directly using heart measurements.

Capture detection is a process by which the effectiveness of current therapy is assessed. Commonly, this involves sensing a signal following each pacing pulse delivered to the heart, then comparing this sensed signal with an expected evoked response signal. Capture detection helps to ensure that the particular approach to dynamic adjustment of pacing energy continues to provide effective therapy. The present invention may be used with any number of capture detection methods and systems, including those not yet developed.

Capture reacquisition is a process by which pacing pulse energy is increased in order to reacquire capture of the heart with the lowest possible energy use. Typically, this involves raising the pacing pulse energy in incremental steps until capture is obtained, pacing the heart at the new energy level for a predefined number of beats to confirm the stability of the new capture threshold, and then setting the output level just above this new pacing pulse energy to introduce a safety margin. Capture reacquisition is commonly used in connection with capture detection to maintain effective pacing therapy despite a patient's changing capture threshold. The present invention may be used with any number of capture reacquisition methods and systems, including those not yet developed, such as those in which a patient's capture threshold is assessed directly using heart measurements.

Regardless of the particular methods employed to dynamically adjust pacing pulse energy in process step 300, once the process adjusts the pacing pulse energy, the control program according to one illustrative embodiment of the present invention is initiated, as represented by the arrow leaving step 300. Following the setting of a new pacing pulse energy, microcontroller 60 identifies the operating parameter(s) that potentially require adjustment in step 305. In one embodiment, step 305 is performed by checking a lookup table in memory 94 to determine which operating parameter(s) might require adjustment. In one embodiment, such a determination is based upon some characteristic of the change in pacing pulse energy, for example, whether the change involved the atrial or the ventricular pacing energy. An example of the types of parameters to be included in such a lookup table are shown in FIG. 4, which is discussed in greater detail below. It will be understood that none, some, or all of the identified operating parameters may require adjustment, with such determination being made based on the degree and/or type of change made in the pacing pulse energy, as is also described in more detail below.

Once microcontroller 60 identifies the parameter(s) that may require adjustment at step 305, it then checks whether any parameters remain to be adjusted in step 310. In one embodiment, the microcontroller 60 checks adjustment flags set in step 305 for the respective operating parameters. In an alternative embodiment, steps 305 and 310 are combined. If no parameters remain to be adjusted, the process returns to process step 300. If parameters remain to be adjusted, control passes to step 315.

In step 315, the next parameter to be adjusted is selected. This selection may be sequential, or may be based upon the particular timing needs of the parameters included in the identified group. Following this, the microcontroller 60 checks in step 320 whether a change is needed for the selected parameter based upon the change in pacing pulse energy. In one embodiment, the microcontroller 60 makes distinctions in step 320 based upon whether the amplitude or the width of the pacing pulse has been changed, and also takes other variables of the device into account. In general, however, the degree and nature of the change in pacing pulse energy is used as the primary factor. If no change is needed, any necessary flags are reset, and control passes back to step 310. If a change is needed, control passes to step 325.

In step 325, the microcontroller 60 adjusts the selected parameter based upon the new pacing energy. In one embodiment, microcontroller 60 changes the parameter using a transformation algorithm, which is based upon pulse amplitude, pulse width, or pulse energy. In addition, the transformation algorithm may be fixed, programmable, or auto-programmable. Following the adjustment of the selected parameter, any necessary flags are reset before control passes back to step 310.

In another embodiment, the microcontroller 60 changes the selected parameter using a lookup table. The lookup table may be generic to a family of pacemakers, or based upon factory calibrations using the individual pacemaker, programmable by the physician, or auto-programmed after implant (e.g., upon appropriate triggering, the implanted device would test all possible output combinations and determine appropriate table values based upon sensed responses). Examples of lookup tables for changing a selected parameter are shown in FIGS. 5, 6, 7 and 8, which are described in more detail below.

For some parameters, a separate table (or other suitable data structure) is preferably provided for each output configuration (i.e. bipolar vs. unipolar), and the microcontroller 60 would also check the output configuration in step 325 before using a table to change the selected parameter. Additionally, in an alternative embodiment, step 320 is combined with step 325.

Although the present invention is described in one illustrative embodiment in terms of adjusting one or more operating parameters based upon changes in pacing pulse energy (pulse width, amplitude, or a combination thereof), it is understood that other variables may also be combined with pacing energy output for determining an adjustment. For example, in one embodiment, the maximum sensor rate (MSR) is related to both the pacing pulse energy and current battery level (FIG. 6).

FIG. 4 is an illustration of two operating parameter groupings that are used by implantable stimulation device 10 according to one embodiment of the invention. Parameter grouping 400 shows examples of operating parameters that may or may not be changed when the atrial pulse energy is adjusted. A first operating parameter 402 is the ventricular blanking period and/or the ventricular safety standby. These parameters may be adjusted to prevent inappropriate pacemaker inhibition, thus improving patient safety, as described in more detail below in connection with FIG. 5.

A second parameter 404 is the maximum sensor rate. This parameter is changed to extend battery life, without compromising effective therapy, as described below in connection with FIG. 6. A third parameter 406 is the ventricular refractory and/or atrial refractory period. These parameters may be changed to prevent over-sensing of far-field responses at high output energies, as described in more detail below in connection with FIG. 7. A fourth parameter 408 is the atrial and/or ventricular sensitivity. These parameters may be changed to prevent over-sensing of pacing artifacts at high output energies, as described below in connection with FIG. 8.

A fifth operating parameter 410 that may be adjusted is atrial lead supervision. This parameter is Boolean (either on or off) and allows a lead supervision algorithm to be disabled at very low pulse energies (where it normally would not work). A sixth operating parameter 412 is atrial fast recharge and/or atrial block overlap. These parameters are changed to allows IEGM and sensing circuits flexibility to prevent transient noise. In general, as the pulse output energy increases, so do the fast recharge and block overlap values, as will be understood by those skilled in the art.

Parameter grouping 450 shows examples of operating parameters that may be changed when the ventricular pulse energy is adjusted. A first parameter 452 is the maximum sensor rate, as described in more detail below in connection with FIG. 6. A second parameter 454 is the PVAB, which may be changed to prevent over-sensing of far-field evoked responses at high output energies, preferably by increasing the atrial blanking period as the pacing output increases. A third parameter 456 is the ventricular refractory and/or atrial refractory period, as described in more detail below in connection with FIG. 7.

A fourth parameter 458 is the atrial and/or ventricular sensitivity, as described below in connection with FIG. 8. A fifth parameter 460 is ventricular lead supervision, which is similar to atrial lead supervision. A sixth parameter 462 is ventricular fast recharge and/or ventricular block overlap, whose values tend to increase with increases in the pacing pulse energy.

FIG. 5 is an illustration of a parameter value table that may be used by implantable stimulation device 10 to adjust the ventricular blanking period in response to changes in the atrial pulse amplitude. While the data is shown as being stored in a look-up or association table, it will be understood that such data may be maintained by device 10 in any suitable manner. In addition, the parameter values in FIG. 5, as well as in FIGS. 6–8, are presented for the purpose of clarity; the values contained therein are only approximations to depict the types of transformations involved.

Referring now to FIG. 5, in one illustrative embodiment the ventricular blanking period values range from 4 to 39 ms, with 39 ms being a typical value at high output settings. Thus, FIG. 5 depicts values that may be used by microcontroller 60 to adjust the ventricular blanking period of implantable device 10 when the atrial pulse amplitude changes.

FIG. 6 is an illustration of a parameter value table that is used by implantable stimulation device 10 to adjust the maximum sensor rate in response to a change in pulse output energy. In one illustrative embodiment, the maximum sensor rate is a function of both the pulse output energy and the battery impedance (which is one measure of the energy remaining in battery 110). As can be readily determined from the table, the maximum sensor rate increases with increased pacing pulse energy and increased battery impedance. This table is equally applicable to atrial and ventricular pacing pulse energy.

FIG. 7 is an illustration of a parameter value table that is used by implantable stimulation device 10 to adjust atrial and ventricular refractory periods in response to changes in the pulse output energy. In one illustrative embodiment, adjustments to the refractory period only begin after the pulse amplitude is set to a level equal to or greater than 4.25 volts. As the pulse amplitude increases above 4.25 volts, the refractory period increases as well. This type of table is also applicable for adjustments to the PVAB.

FIG. 8 is an example of a parameter value table that is used by implantable stimulation device 10 to adjust sensitivity settings in response to changes in pulse output energy. In one embodiment, a sensitivity setting is adjusted based upon the pulse amplitude. This type of table is equally applicable to either atrial or ventricular chambers of the heart. As the pulse amplitude increases, the sensitivity level increases, thereby requiring the sensing of larger signals before device 10 will respond to the signal.

For these and other parameters, various equations, functions, or tables may be used to determine a new setting for an operating parameter based upon a change in pulse output energy. For example, for lead supervision, a function may be employed that disables lead supervision when the pacing pulse energy drops below a certain level, for example, 0.375 volts. Those skilled in the art will understand the various options available for the programmable parameters discussed, as well as others not discussed, given the disclosure herein.

Therefore, while various embodiments of the present invention have been described above, it should be understood that they have been presented by way of example only, and not limitation. It is to be understood that the description and drawings represent the presently preferred embodiment(s) of the invention and are, as such, representative of the subject matter which is broadly contemplated by the present invention.

Furthermore, the scope of the present invention fully encompasses other embodiments that may become obvious to those skilled in the relevant art(s). Thus, the breadth and scope of the present invention should not be limited by any of the above-described exemplary embodiments, but should be defined only in accordance with the issued claims and their equivalents.

What is claimed is:

1. A method for operating an implantable cardiac stimulation device, the method comprising:
   dynamically modifying a pacing pulse energy;
   determining whether one or more operating parameters, other than pacing pulse width and pacing pulse amplitude, require adjustment in response to a change in the pacing pulse energy; and
   adjusting a value for an operating parameter to a new value if the operating parameter requires adjustment, wherein the new value is based upon the pacing pulse energy;
   wherein the one or more operating parameters comprise at least one of a blanking period, a safety standby, a maximum sensor rate, a refractory period, a lead supervision, a fast recharge, and a block overlap.

2. The method of claim 1, wherein the pacing pulse energy comprises one of an atrial pacing pulse amplitude and a ventricular pacing pulse amplitude.

3. The method of claim 1, wherein automatically adjusting a value comprises:
   determining a characteristic of the pacing pulse energy being changed;
   determining one or more corresponding operating parameters based on the characteristic of the pacing pulse energy being changed;
   determining one or more new values for the one or more operating parameters; and
   storing the one or more new values in an appropriate memory location.

4. The method of claim 1, wherein the change in the pacing pulse energy comprises an atrial or a ventricular pacing pulse energy.

5. The method of claim 3, wherein determining one or more new values for the one or more operating parameters comprises determining the one or more new values based on the magnitude of the pacing pulse energy.

6. The method of claim 1, wherein the dynamically modifying a pacing pulse energy is performed during a capture threshold test.

7. The method of claim 1, wherein the dynamically modifying a pacing pulse energy is performed during autocapture.

8. A method for operating an implantable cardiac stimulation device, the method comprising:
   dynamically modifying a pacing pulse energy;
   determining an operating parameter to adjust based upon a characteristic of the pacing pulse energy that is changed, the operating parameter being other than pacing pulse amplitude and pacing pulse width;
   determining a new value for the operating parameter based upon the new pacing pulse energy; and
   storing the new value in a memory location associated with the operating parameter;
   wherein the operating parameter comprise at least one of a blanking period, a safety standby, a maximum sensor rate, a refractory period, a lead supervision, a fast recharge, and a block overlap.

9. The method of claim 8, wherein determining a new value comprises: accessing an operating parameter table and determining a corresponding value for the operating parameter based on the pacing pulse energy level.

10. The method of claim 8, wherein determining a new value comprises calculating the new value using a function associated with the operating parameter.

11. The method of claim 8, wherein the dynamically modifying a pacing pulse energy is performed during a capture threshold test.

12. An implantable stimulation device comprising:
   a pulse generator that generates stimulation pulses;
   cardiac sensing circuitry that generates sense signals; and
   a control unit coupled with the pulse generator and the cardiac sensing circuitry, the control unit being configured to:
      determine a capture threshold based on one or more signals from the sensing circuitry;
      adjust a pacing pulse output energy in response to a change in capture threshold; and
      modify a value for one or more operating parameters when the pacing pulse output energy has been changed, wherein the one or more operating parameters are other than pacing pulse width and pacing pulse amplitude, wherein a new value is based upon a new pacing pulse energy; and wherein the one or more operating parameters comprise at least one of a blanking period, a safety standby, a maximum sensor rate, a refractory period, a lead supervision, a fast recharge, and a block overlap.

13. The implantable stimulation device of claim 12, wherein the control unit comprises a microcontroller and a control program, and wherein the implantable stimulation device further comprises a memory.

14. The implantable stimulation device of claim 13, wherein the control program causes the microcontroller to perform the modifying operation by:
   checking the memory to determine whether auto-adjustment of the operating parameter is enabled;
   determining the new value for the operating parameter if auto-adjustment of the operating parameter is enabled; and
   storing the new value in a memory location in the memory that is associated with the operating parameter.

15. The implantable stimulation device of claim 13, wherein the control program causes the microcontroller to determine the new value by:
   converting the new pacing pulse energy into an array index; and
   using the array index to identify an element of an array containing the new value, wherein the array is associated with the operating parameter.

16. The implantable stimulation device of claim 15, wherein the elements of the array are programmable.

17. The implantable stimulation device of claim 13, wherein the control program causes the microcontroller to determine the new value by calculating the new value using a function associated with the operating parameter.

18. The implantable stimulation device of claim 17, wherein the function associated with the operating parameter is programmable.

19. The implantable stimulation device of claim 12, wherein the pacing pulse energy comprises an atrial pacing pulse amplitude.

20. An implantable stimulation device comprising:
   means for generating a stimulation pulse having a pulse energy level;
   means for sensing cardiac activity;
   means for modifying the pulse energy level; and
   means for adjusting a value for an operating parameter when the pulse energy level has been modified, wherein the operating parameter is other than pacing pulse width and pacing pulse amplitude, wherein the adjusted value is based upon the modified pulse energy level; and wherein the operating parameter comprises at least one of a blanking period, a safety standby, a maximum sensor rate, a refractory period, a lead supervision, a fast recharge, and a block overlap.

21. The implantable stimulation device of claim 20, wherein the means for modifying the pulse energy level is performed during a capture threshold test.

22. The implantable stimulation device of claim 20, wherein the means for modifying the pulse energy level is performed during autocapture.

* * * * *